US006153373A

United States Patent [19]

Benjamin et al.

[11] Patent Number: 6,153,373
[45] Date of Patent: Nov. 28, 2000

[54] METHOD FOR SEX DETERMINATION OF MAMMALIAN OFFSPRING

[75] Inventors: Thomas L. Benjamin, Cambridge; Barbara Kohn, Watertown; Christopher J. Basker, Mansfield; Susan George, Chelmsford; David Livingston, Brookline, all of Mass.

[73] Assignee: Vicam, L.P., Watertown, Mass.

[21] Appl. No.: 09/299,181

[22] Filed: Apr. 23, 1999

Related U.S. Application Data

[63] Continuation of application No. 08/886,203, Jul. 1, 1997.

[51] Int. Cl.[7] .............................. A01N 1/02; C12N 5/06; G01N 33/538; C07K 16/28
[52] U.S. Cl. ............................. 435/2; 435/325; 435/374; 436/538; 436/541; 530/387.1; 530/391.1; 530/852
[58] Field of Search ................................ 436/538, 541; 435/2, 325, 374; 530/387.1, 391.1, 852

[56] References Cited

U.S. PATENT DOCUMENTS

| | | |
|---|---|---|
| 3,906,929 | 9/1975 | Augspurger . |
| 4,083,957 | 4/1978 | Lang . |
| 4,085,205 | 4/1978 | Hancock . |
| 4,191,749 | 3/1980 | Bryant . |
| 4,230,685 | 10/1980 | Senyei et al. ............................. 424/12 |
| 4,362,246 | 12/1982 | Adair . |
| 4,448,767 | 5/1984 | Bryant . |
| 4,474,875 | 10/1984 | Shrimpton . |
| 4,680,258 | 7/1987 | Hammerling et al. . |
| 4,722,887 | 2/1988 | Fabricant et al. . |
| 4,769,319 | 9/1988 | Ellis et al. . |
| 4,770,992 | 9/1988 | Van den Engh et al. . |
| 4,999,283 | 3/1991 | Zavos et al. . |
| 5,021,244 | 6/1991 | Spaudling . |
| 5,108,933 | 4/1992 | Liberti et al. ............................. 436/501 |
| 5,186,827 | 2/1993 | Liberti et al. . |
| 5,200,084 | 4/1993 | Liberti et al. . |
| 5,225,282 | 7/1993 | Chagnon et al. . |
| 5,389,377 | 2/1995 | Chagnon et al. . |
| 5,466,574 | 11/1995 | Liberti et al. . |
| 5,660,997 | 8/1997 | Spaulding . |

FOREIGN PATENT DOCUMENTS

| | | |
|---|---|---|
| 1148082 | 6/1983 | Canada . |
| 20213391 | 3/1987 | European Pat. Off. . |
| 20251710 | 1/1988 | European Pat. Off. . |
| WO84/01265A1 | 4/1984 | WIPO . |

OTHER PUBLICATIONS

D.L. Garner, Proceedings of the Tenth Technical Conference on Artificial Insemination and Reproduction, Apr. 12–14, 1984, pp. 87–92, "An Overview of Separation of X–and Y–Spermatozoa".
D. Pinkel et al., Journal of Animal Science, vol. 60, No. 5, pp. 1303–1307 (1985).
B. Brandriff et al., Fertility and Sterility, vol. 46, No. 4, pp. 678–685 (Oct. 1986).
Hoppe and Koo (1984) J. Reproductive Immunology vol. 5, pp. 109.
Reacting mouse sperm with monoclonal H–Y antibodies does not influence sex ratio of eggs fertilized in vitro.
Ali, Eldridge, Koo and Schanbacher (1990)Arch, of Andrology vol. 24, pp. 235–245.
Enrichment of Bovine X–and Y–Chromosome–Bearing sperm with Monoclonal H–Y Antibody–Flourescence–Activated Cell Sorter.
Peter, AT et al. Theriogenology. 40:1177–1185, 1993.

*Primary Examiner*—David Saunders
*Assistant Examiner*—F. Pierre VanderVegt
*Attorney, Agent, or Firm*—Birch, Stewart, Kolasch & Birch, LLP

[57] ABSTRACT

A method for increasing the percentage of mammalian offspring of either sex which comprises contacting a semen sample with an antibody specific for the spermatozoa determinative of one sex and separating said spermatozoa from spermatozoa determinative of the other sex, said antibody being bound to a non-porous magnetic bead support having a diameter of 0.1 to 2 microns.

10 Claims, No Drawings

METHOD FOR SEX DETERMINATION OF MAMMALIAN OFFSPRING

This application is a continuation of co-pending Application No. 08/886,203, filed on Jul. 1, 1997, the entire contents of which are hereby incorporated by reference.

BACKGROUND AND FIELD OF THE INVENTION

The present invention is directed to a method for increasing the percentage of mammalian offspring of either sex by contacting a sperm sample with an antibody specific for one sex, the antibody being bound to a magnetic bead of a diameter which permits separation of spermatozoa having sufficient motility to permit successful insemination and fertility.

Farmers and other animal husbandry persons have long recognized the desirability of enhancing the probability of offspring of a selected sex. Methods have been proposed in the past for increasing the percentage of X-sperm cells or Y-sperm cells to thereby achieve a greater chance of achieving male or female offspring, respectively. Examples of prior research are reviewed, for example, in Garner, D. L. et al., "An Overview of Separation of X- and Y-Spermatozoa," *Proceedings of the Tenth Technical Conference on Artificial Insemination and Reproduction* (National Association of Animal Breeders), pp. 87–92 (1984) and Pinkel, D. et al., "Flow Cytometric Determination of the Proportions of X- and Y-Chromosome Bearing Sperm In Samples of Purportedly Separated Bull Sperm," *J. Animal Scien.*, 60, pp. 1303–1307 (1985).

Previous methods have included, for example, methods based upon density sedimentation (see, for example, Brandriff, B. F. et al. "Sex Chromosome Patios Determined by Karyotypic Analysis in Albumin-Isolated Human Sperm," *Fertil. Steril.*, 46, pp. 678–685 (1986))

U.S. Pat. No. 3,687,806 to Van Den Bovenkamp discloses an immunological method for controlling the sex of mammalian offspring by use of antibodies which react with either the X- or Y-chromosomes and utilizing an agglutination step to separate bound antibodies from unaffected antibodies.

U.S. Pat. No. 4,191,749 to Bryant discloses a method for increasing the percentage of mammalian offspring of either sex by use of a male-specific antibody coupled to a solid-phase immunoabsorbant muateria to selectively bind male-determining spermatozoa, while the female-determining spermatozoa remain unbound in a supernatant.

U.S. Pat. No. 5,021,244 to Spaulding discloses a method for sorting living cells based upon DNA content, particularly sperm populations to produce subpopulations enriched in X- or Y-sperm by means of sex-associated membrane proteins and antibodies specific for such proteins.

However, these methods often result in insufficient separation of X- and Y-sperm and often damage the sperm, thereby reducing its motility and fertility success rate.

SUMMARY OF INVENTION

It is, therefore, an object of the present invention to provide a method for increasing the probability that mammalian offspring will be of a specific desired sex.

It is a further object of the invention to provide a method for the separation of X- and Y-determinative spermatozoa without compromising the motility or fertilization rate of the separated spermatozoa.

It is another object of the present invention to provide a method for artificial insemination which permits insemination with a sperm sample enriched in X- or Y-determinative sperm.

It is still a further object of the invention to provide a method for separating X- and Y-determinative sperm by means of antibodies specific for the selected sperm, bound to magnetic beads, to permit highly specific separation, so as to provide a sperm sample enriched in one selected spermatozoa type and substantially free of the other spermatozoa type.

These and further objects of the present invention are achieved by a method which contacts a sperm sample with antibodies specific to a selected spermatozoa type, the antibodies being bound to beads, preferably magnetic beads having a diameter of from 0.1 to 2 microns, and subsequently removing the beads whereby the remaining supernatant may be collected and contains spermatozoa of only X- or Y-determinative type.

DETAILED DESCRIPTION OF THE INVENTION

The present invention provides for separation of X- and Y-bearing sperm which are competent to fertilize using standard AI techniques. As noted above, prior methods of separation often compromise the motility and fertilization ability of the sperm, so that fertilization utilizing such separated sperm requires complicated techniques such aa IVF. The method of the invention can be utilized for separating X- and Y-sperm from a variety of mammalian species, including various livestock, such as cattle and sheep, as well as dogs, cats, horses, swine, and other species. The process is also applicable to humans.

By means of the present invention, a sperm sample containing both X- and Y-sperm can be separated to produce an X- or Y-enriched sperm subpopulation which is substantially pure with respect to the desired spermatozoa and substantially free of the other spermatozoa-type. By "substantially free," we mean that use of a sample enriched, for example, with X-sperm, when utilized for artificial insemination, has only a small chance of producing male offspring, because the sperm sample has less than 20%, preferably less than 10%, of Y-sperm. Separation of the X- or Y-spermatozoa is accomplished by use of antibodies which bind to X- or Y-specific proteins from sperm cells. These antibodies can be of any type of antibody (including IgG and IgM) and can be either polyclonal antibodies or monoclonal antibodies. If polyclonal antibodies are to be used, then such antibodies can be prepared according to per se known procedures. For example, procedures such as those described in Hurn, B.A. et al., (1980), *Meth. in Enzymolocy*, Ed. Van Vanakis, H. and Langone, J., pp. 10414 142, can be used.

If desired, monoclonal antibodies can be utilized and prepared according to methods which are per se known in the art, such as those originally authored by Milstein and Kohler, published in *Nature* (1975), 256, pp. 495–497. This basic procedure involves injecting an animal, usually a mouse, with an immunogenic substance. After suitable time for antibody production to the immunogen, the mouse is sacrificed. Cells are removed from the spleen and fused with myeloma cells. Hybridoma cells resulting from this fusion are able to reproduce in vitro, and each express a genetic information for one specific antibody. The antibodies produced from one hybridoma fusion thus will only recognize a single antigenic determinative of the immunogen.

Cells cultured from individual hybridoma cells can then be screened for production of antibodies to the target antigenic determinant. Those hybridomas positive for the target antigen can be further screened to identify those having the desired level of affinity.

Monoclonal antibodies displaying all of these characteristics can then be screened using actual assay conditions to determine if the assay condition alters the antibody binding characteristics or affinity, and to screen out those with cross-reactivity to possible contaminating antigens.

Preferred antibodies are those which are specific for and bind to Y-sperm, such as antibodies which bind to the H-Y antigen. Such antibodies can be prepared, for example, by the procedure described in U.S. Pat. No. 4,680,258 to Hammerling et al.

As noted above, the antibodies specific for either X- or Y-spermatozoa are immobilized on beads. These beads can be plastic beads or magnetic beads. Useful plastic beads are Sepharose 6MB, or other beads which are large enough to settle out in a batch purification process. When plastic beads are utilized, the beads having antibody bound thereto are mixed in a sperm sample and allowed to settle to the bottom of the container. This step can be repeated, if desired, to increase the completeness of separation of sperm according to sex chromosome.

If magnetic beads are used, the beads are microspheres of magnetic particles representing an immobilizing matrix. It has been found, according to the present invention, that magnetic beads having a diameter of from 0.1 to 2 microns in diameter are specifically useful for separating the desired species of spermatozoa without compromising the motility and fertilization ability of the spermatozoa. Particularly useful magnetic beads are described, for example, in U.S. Pat. No. 5,071,076; U.S. Pat. No. 5,108,933; U.S. Pat. No. 4,795,698; and PCT Pat. No. Publication No. WO91/09678. According to the procedures described in these patents, beads can be prepared having especially a diameter of 0.1 to 0.5 microns.

The antibodies are bound to the beads by means of procedures which are per se known in the art. In general, a linking compound is attached to the magnetic beads during manufacture of the beads. On to the beads, an antibody (such as an IgG antibody which is directed against mouse IgM) is bound by mixing beads at about 1 mg iron/ml with purified antibody at 1 mg/ml protein. After the antibody is bound to the beads, the beads are washed so only attached antibody remains. Additional procedures known to those skilled in the art are described, for example, in U.S. Pat. No. 4,018,886; U.S. Pat. No. 3,970,518; U.S. Pat. No. 4,855,045; and U.S. Pat. No. 4,230,685. Protein A is a preferred linking compound which greatly increases the effectiveness of capture by the attached antibodies. (Forsgren et al., (1977) *J. Immunol.* 99:19). Protein A attaches to the Fc portion of IgG subclass antibodies, thus extending and presenting the Fab portion of these antibodies. The resulting correct orientation of the antibodies and extension away from the particles leads to a very effective interaction between the bound antibodies and their target.

The method of attachment of Protein A to magnetic particles may proceed by any of several processes available through known scientific literature. In one such procedure, magnetic iron oxide particles of approximately one micrometer diameter are chemically derivatized by a reaction, first with 3-aminopropyltriethoxysilane, then with glutaraldehyde. The derivatized magnetic particles are then mixed with Protein A resulting in a magnetic particle to which Protein A is covalently attached. The antibodies are then added to the Protein A magnetic particles and after a short incubation, the Protein A-antibody complexes form. (Weetall, H.H. (1976) *Meth. In Enzymol.* 44:134–48).

The following is a specific example of the method according to the invention.

EXAMPLE 1

About $10^8$ to $10^{10}$ spermatozoa in amount 1–10 ml of volume are washed with buffered culture medium (Dulbeco's Modified Eagles Medium) by centrifuging at 1,500 rpm for 10 minutes. The sperm are then resuspended in 4 ml buffered culture medium after gently decanting the supernatant. The sperm suspension is then divided into two vials, and into each vial is added 500 $\mu$L of magnetic beads having bound thereto antibodies for Y-bearing sperm. The vials are capped and then rotated at 3 rpm, end over end, on a rotator at room temperature for 30 minutes.

After rotation, the caps are loosened and placed in a magnetic capture rack, such as that described in U.S. Pat. No. 5,571,481. After 15 minutes of exposure to the magnetic field, the supernatant is removed which is rich in X-bearing sperm and substantially free of Y-bearing sperm. The removed supernatant is then counted for sperm, and the concentration is adjusted as necessary for insemination. That sample is then loaded into a straw or straws for the insemination procedure.

If desired, more complete separation can be obtained by repeating, in a serial manner, the magnetic capture procedure on the supernatant.

Each of the publications/patents referred to above is hereby incorporated by reference.

The invention being thus described, it will be clear that the same may be varied in many ways. Such variations are not to be regarded as a departure from the spirit and scope of the invention, and all such modifications as would be obvious to one skilled in the art are intended to be included within the scope of the following claims.

What is claimed is:

1. A method of increasing the percentage of mammalian offspring of either sex which comprises contacting a semen sample with an antibody specific for the spermatozoa determinative of one sex and separating said spermatozoa from spermatozoa determinative of the other sex, said antibody being bound to a non-porous magnetic bead support having a diameter of 0.1 to 2 microns.

2. The method according to claim 1, wherein said antibody is bound to said beads through an intermediate linking compound.

3. The method according to claim 2, wherein said intermediate linking compound is Protein A.

4. The method according to any one of claims 1–3, wherein said antibody is specific for Y-bearing sperm.

5. The method according to claim 4, wherein said antibody is specific for an H-Y antigen.

6. The method according to claim 4, wherein said beads have a diameter of 0.1 to 0.5 microns.

7. The method according to claim 6, wherein said antibody is a monoclonal antibody.

8. The method according to claim 1, wherein said semen sample is contacted with said beads, the sample is exposed to a magnetic field, and the remaining supernatant is removed to provide a supernatant rich in X-bearing sperm.

9. The method according to any one of claims 1–3 and 8, wherein said supernatant rich in X-bearing sperm is subjected to said method at least one additional time.

10. The method according to claim 4, wherein said supernatant rich in X-bearing sperm is subjected to said method at least one additional time.

* * * * *